United States Patent [19]

Shimokawa et al.

[11] Patent Number: 4,708,821

[45] Date of Patent: Nov. 24, 1987

[54] PROCESS FOR PREPARING AQUEOUS GEL AND USE THEREOF

[75] Inventors: Wataru Shimokawa, Hachioji; Katuaki Fukumori, Nagareyama, both of Japan

[73] Assignee: Hoechst Gosei Kabushiki Kaisha, Tokyo, Japan

[21] Appl. No.: 843,430

[22] Filed: Mar. 24, 1986

[30] Foreign Application Priority Data

Mar. 27, 1985 [JP] Japan .................................. 60-62690
Jul. 6, 1985 [JP] Japan .................................. 60-149015
Nov. 11, 1985 [JP] Japan .................................. 60-252488

[51] Int. Cl.$^4$ ............................ A61K 7/46; C11B 9/00
[52] U.S. Cl. .................................... 512/12; 252/315.3; 252/315.4; 252/49.5; 512/27
[58] Field of Search .................... 252/522 A, 522 R

[56] References Cited

U.S. PATENT DOCUMENTS

| | | | |
|---|---|---|---|
| 3,472,940 | 10/1969 | Osipow et al. | 252/522 A |
| 3,954,963 | 5/1976 | Kuderna et al. | 252/522 A |
| 3,954,964 | 5/1976 | Kuderna et al. | 252/522 A |
| 3,997,480 | 12/1976 | Singleton et al. | 252/522 A |
| 4,067,824 | 1/1978 | Teng et al. | 252/522 A |
| 4,128,507 | 12/1978 | Mitzner | 252/522 A |
| 4,362,841 | 12/1982 | Minatono et al. | 252/522 A |
| 4,561,997 | 12/1985 | Roehi | 252/522 A |
| 4,587,129 | 5/1986 | Kliment | 252/522 A |

FOREIGN PATENT DOCUMENTS

| | | | |
|---|---|---|---|
| 3015460 | 10/1980 | Fed. Rep. of Germany | 252/522 A |
| 0166168 | 10/1982 | Japan | 252/522 A |
| 0025753 | 2/1984 | Japan | 252/522 A |
| 0025754 | 2/1984 | Japan | 252/522 A |

*Primary Examiner*—Werren B. Lone
*Attorney, Agent, or Firm*—Armstrong, Nikaido, Marmelstein & Kubovcik

[57] ABSTRACT

A process for preparing an aqueous gel which comprises mixing a water-soluble acetoacetylated high molecular compound, a cross-linking agent and water, thereby cross-linking said high molecular compound to form an aqueous gel. According to the process of the invention, an aqueous gel having excellent transparency and small serum-separation, can be prepared at room temperature by only mixing. Also, according to the present invention, there are provided the aqueous gel composition containing perfume or deodorant, and the lubricant and the method for use thereof, which utilizes the process of claim 1.

12 Claims, No Drawings

PROCESS FOR PREPARING AQUEOUS GEL AND USE THEREOF

BACKGROUND OF THE INVENTION

The present invention relates to a process for preparing an aqueous gel which can be prepared at room temperature and has an excellent transparency and a remarkably small separation of water at low temperature as well as at high temperature.

Also, the present invention relates to an improved aqueous gel composition containing perfume or deodorant, in which a perfume used for giving out fragrance or annuling smell is contained in the aqueous gel prepared by utilizing the above-mentioned process. The aqueous gel composition is placed indoors or the inside of a car and the effect of the aqueous gel composition is kept for a long period.

Further, the present invention relates to a lubricant for metal-processing, which is used when metals are rolled, pulled out or cut under cooling or heating, and a method for use thereof.

Several percents by weight of agar is added to water and is dissolved in water with heating. The aqueous solution is cooled to form an aqueous gel in the form of a pudding. An aqueous gel can be obtained in the same manner as in the above-mentioned method by using gelatine, alginic acid, carrageenan, or the like instead of agar.

However, the above-mentioned natural gels require a step of heat-dissolveing. Moreover the obtained gel is fragile and weak, and is remarkably poor in transparency. Also, gelatine has glue odor. An aqueous gel also is obtained by adding boric acid or borax to aqueous polyvinyl alcohol solution, but the aqueous gel is remarkably weak and has a defect that the gel releases water (hereinafter referred to as "serum-separation") by freeze and thaw, maintaining at high temperature for a long period, or repetition of freezing and heating to high temperature. Also, the aqueous gel has a defect that the partial gelation occurs easily, and therefore it is difficult to obtain a uniform aqueous gel.

An object of the present invention is to provide a process for preparing an aqueous gel, which can solve the above-mentioned defects.

As an aqueous gel composition containing perfume, a composition prepared by dispersing a perfume into a conventional aqueous gel such as carrageenan, agar, or the like, is mainly used.

However, the conventional aqueous gel composition has the following defects.

(1) The gelation of the composition is carried out by dissolving the perfume in the aqueous gel with heating at 60° to 80° C. and cooling it at room temperature. Therefore, perfumes having a poor heat-resistance are deteriorated by heating.

(2) The conventional aqueous gel per se is poor in transparency.

(3) The redissolution or the serum-separation phenomenon occurs at a temperature of more than about 50° C.

(4) The decrease of gel strength or the serum-separation phenomenon occurs at low temperature.

Another object of the present invention is to provide an aqueous gel composition containing perfume or deodorant, which can be solved the above-mentioned defects, by utilizing the process for preparing an aqueous gel of the invention.

In general, as a lubricant for metal-processing, a mixture of graphite and oil, a metal soap, or the like is used and in order to improve the adhesion of the lubricant, mainly, a polymer such as a synthetic resin emulsion is added to the lubricant. A lubricant is coated on a steel plate to be processed and dried to form a lubricous film. The lubricant including a synthetic resin emulsion requires a lot of time for drying.

When drying is carried out at high temperature for rapid drying, the foaming phenomenon occurs, and accordingly, it is hard to obtain a uniform film. On the other hand, when drying is carried out at low temperature, the drying time is prolonged and the drying line is lengthened, thus resulting in practical disadvantage.

Further objects of the present invention are to provide a lubricant for metal-processing, which can solve the above-mentioned defects, by utilizing the process for preparing an aqueous gel of the invention and to provide a method for use thereof.

SUMMARY OF THE INVENTION

The present inventors have earnestly studied with respect to an aqueous gel in order to solve the above-mentioned defects. As a result, the present inventors have found that various aqueous solutions of water-soluble acetoacetylated high molecular compounds rapidly gel with a specific cross-linking agent at room temperature to form a transparent aqueous gel, and have accomplished the present invention.

That is, in accordance with the present invention, there is provided a process for preparing an aqueous gel, which comprises mixing a water-soluble acetoacetylated high molecular compound, a cross-linking agent and water, thereby forming cross-linking network structure between the high molecular compounds to form an aqueous gel, and the excellent gel can be obtained by means of an extremely easy operation, that is, by mixing method at room temperature.

Also, the present inventors have found that the defects of the conventional aqueous gel composition containing perfume or deodorant can be solved by utilizing the process for preparing aqueous gel of the invention. That is, in accordance with the present invention, there is provided an aqueous gel composition containing perfume of deodorant comprising an aqueous gel prepared by mixing a water-soluble acetoacetylated high molecular compound, especially acetoacetylated polyvinyl alcohol, a cross-linking agent and water, thereby forming cross-linking network structure between the high molecular compounds to form an aqueous gel and a perfume or deodorant component. The aqueous gel composition of the invention is excellent in transparency, serum-separation resistance, fresh smell, and the like. Further, the perfume or deodorant aqueous gel composition of the invention can solve the defect that the perfume or deodorant is unevenly given out by including water-soluble alcohols in the aqueous gel composition.

Further, the present inventors have found that the defects of the conventional lubricant for metal-processing can be solved by utilizing the process for preparing an aqueous gel of the invention.

In accordance with the present invention, there is provided a lubricant for metal-processing comprising an aqueous solution of acetoacetylated high molecular compound, especially acetoacetylated polyvinyl alcohol to which a solid lubricant may be added as occasion demands, and an aqueous solution of a cross-linking agent.

In accordance with the invention, there is provided a method for use of the lubricant of the invention, which comprises coating either an aqueous solution of the acetoacetylated high molecular compound or an aqueous solution of the cross-linking agent onto the surface of a metal material to be processed or a metal working tool and then coating the other thereon, or coating these solutions with mixing them onto the surface, to form a lubricous gel film.

DETAILED DESCRIPTION

The instant specification illustrates firstly the process for preparing an aqueous gel, secondarily, the improved aqueous gel composition containing perfume or deodorant, which prepared by utilizing the process for preparing an aqueous gel of the invention, and finally the lubricant for metal-processing prepared by utilizing the process for preparing an aqueous gel of the invention and the method for use of the lubricant.

Examples of the water-soluble high molecular compound used in the invention are, for instance, polyvinyl alcohol, hydroxyethyl cellulose, hydroxypropyl cellulose, methyl cellulose, a carboxymethyl cellulose, starch, and the like. In the process for preparing an aqueous gel of the invention, a water-soluble acetoacetylated high molecular compound is employed. The acetoacetylated compounds may be employed alone or in the admixture thereof.

As a process for acetoacetylating the high molecular compound, for instance in case of employing polyvinyl alcohol as the high molecular compound, there are a process in which polyvinyl alcohol is dispersed in acetic acid as a medium and diketene having the formula:

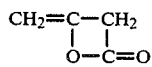

is added to the dispersion, a process in which polyvinyl alcohol is previously dissolved in a medium such as dimethylformaldehyde or dioxane and diketene is added to the solution, and a process in which gaseous or liquid diketene is directly contacted with polyvinyl alcohol.

The water-soluble acetoacetylated high molecular compound has a degree of acetoacetylation of 1 to 15% by mole, preferably 2 to 12% by mole. When the degree of acetoacetylation is less than 1% by mole, it is hard to obtain an aqueous gel, because the cross-linking reaction is hard to proceed. On the other hand, when the degree of acetoacetylation is more than 15% by mole, a water-soluble high molecular compound is hard to dissolve in water depending upon a kind of the compound.

As a cross-linking agent used in the present invention, there are exemplified, a compound containing amino group, a compound containing an aldehyde group, a compound containing hydrazino group, a compound containing epoxy group, a compound containing methylol group, and an alkoxide or chelate compound of metal such a titanium, zirconium or aluminium. These cross-linking agents may be employed alone or in the admixture thereof.

In the invention, as the cross-linking agent containing amino group, there are preferably employed a polyethyleneimine having the formula:

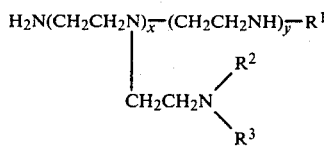

wherein $R^1$, $R^2$ and $R^3$ are the same or different and each is H or $-CH_2CH_2NH_2$ and x and y are the same or different and each is an integer and a molecular weight of 100 to 100,000; a chain aliphatic polyamine such as diethylenetriamine or triethylenetetramine; a cyclic aliphatic polyamine such as menthenediamine or isophoronediamine and a derivative or modified compound thereof; an aromatic polyamine such as methaphenilenediamine or diaminodiphenylsulfone, and a modified compound thereof; an aliphatic polyamidoamine; and an aminosilane compound such as N-β(aminoethyl)γ-aminopropyltrimethoxysilane or γ-aminopropyltrimethoxysilane.

In the invention, as the cross-linking agent containing aldehyde group, for instance, there are suitably used monoaldehydes such as formaldehyde, acetoaldehyde, propionaldehyde, crotonealdehyde, benzaldehyde and formamide; dialdehydes such as glyoxal, malonedialdehyde, glutaraldehyde and terephthalaldehyde; and an acrylic resin copolymerized with acrolein. Among them, glyoxal and glutaraldehyde are preferable.

In the invention, compounds containing two or more hydrazino groups are preferably used as the cross-linking agent containing hydrazino group. For instance, there are exemplified a dihydrazide compound, an organic salt such as a dihydrazide compound of formic acid, oxalic acid, or the like; a monosubstituted dihydrazide compound having a substituent such as methyl, ethyl, propyl, butyl or allyl group; an unsymmetrical disubstituted dihydrazide compound having a substituent such as 1,1-dimethyl, 1,1-diethyl or 4-n-butylmethyl group; a symmetrical disubstituted dihydrazide compound having a substituent such as 1,2-dimethyl, 1,2-diethyl or 1,2-diisopropyl group. Examples of the preferable hydrazide compounds are, for instance, carbohydrazide, oxalic acid dihydrazide, malonic acid dihydrazide, succinic acid dihydrazide, adipic acid dihydrazide, sebacic acid dihydrazide, dodecanoic diacid dihydrazide, isophthalic acid dihydrazide, terephthalic acid dihydrazide, glycolic acid dihydrazide, polyacrylic acid hydrazide, and the like.

In the invention, compounds containing two or more epoxy groups are preferably used as the cross-linking agent. Examples of such epoxy compounds are, for instance, ethyleneglycol glycidyl ether, polyethyleneglycol glycidyl ether, propyleneglycol glycidyl ether, polypropyleneglycol glycidyl ether, neopentylglycol glycidyl ether, glycerol glycidyl ether, trimethylol propaneglycidyl ether, pentaerythritol glycidyl ether, diglycerol glycidyl ether, sorbitol glycidyl ether, bisphenol A/epichlorohydrine-epoxy resin, and the like.

In the invention, an initial condensate of urea resin and an initial condensate of melamine resin are preferably used as the cross-linking agent containing methylol group.

In the invention, examples of the metal alkoxide used as the cross-linking agent are, for instance, tetraethyl titanate, tetrapropyl titanate, tetrabutyl titanate, tetra-2-ethylhexyl titanate, tetraethyl zirconate, tetrapropyl zirconate, tetrabutyl zirconate, tetra-2-ethylhexyl zirconate, aluminium isopropylate, mono-sec-butoxy aluminium diisopropylate, aluminium-sec-butylate, and the like.

In the invention, examples of the metal chelate preferably used as the cross-linking agent are, for instance, titanium lactate, di-i-propoxy bis(acetylacetone)titanate, di-n-butoxy.bis(triethanolamine)titanate, tetraoctylglycol titanate, zirconium tetraacetyl acetonate, ethylacetoacetate aluminium diisopropylate, aluminium tris(ethylacetoacetate), and the like.

It is assumed that the water-soluble high molecular compound having acetoacetyl group in its molecule and the amino group-containing compound form the following cross-linking structure as shown by the following reaction mechanism, thus the compound forms an aqueous gel by including water therein.

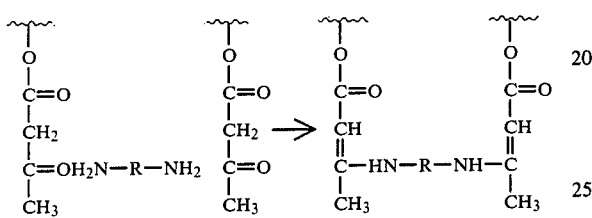

It is assumed that the water-soluble high molecular compound having acetoacetyl group in its molecule and the aldehyde group-containing compound form the following cross-linking structure as shown by the following reaction mechanism, thus the compound forms an aqueous gel by including water therein.

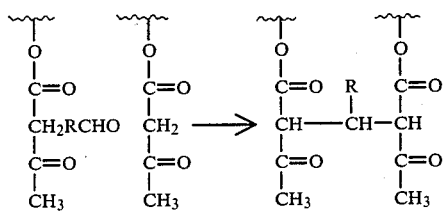

It is assumed that the water soluble high molecular compound having acetoacetyl group in its molecule and the hydrazino group-containing compound form the following cross-linking structure as shown by the following reaction mechanism, thus the compound forms an aqueous gel by including water therein.

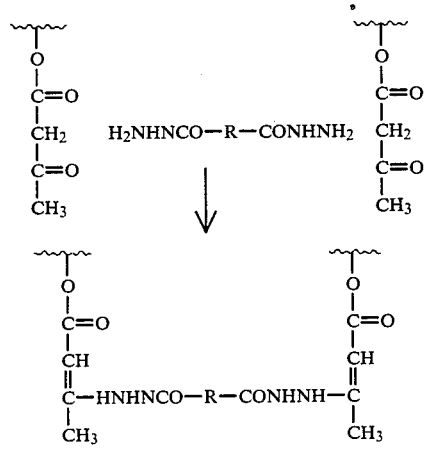

It is assumed that the water-soluble high molecular compound having acetoacetyl group in its molecule and the epoxy group-containing compound form the following cross-linking structure as shown by the following reaction mechanism, thus compound forms an aqueous gel by including water therein.

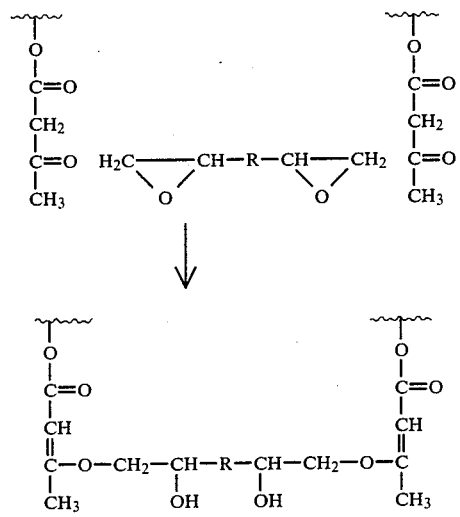

It is assumed that the water-soluble high molecular compound having acetoacetyl group in its molecule and the methylol group-containing compound form the following cross-linking structure as shown by the following reaction mechanism, thus the compound forms an aqueous gel by including water therein.

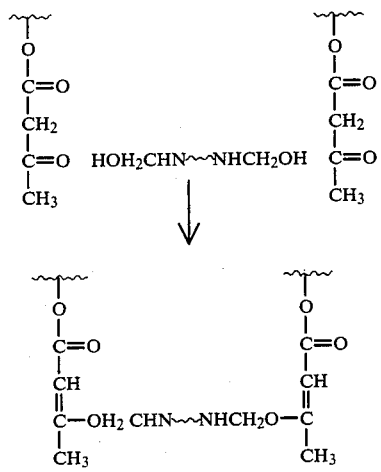

It is assumed that the water-soluble high molecular compound and the metal alkoxide or the metal chelate form the following cross-linking structure as shown by the following reaction mechanism, thus the compound forms an aqueous gel by including water therein.

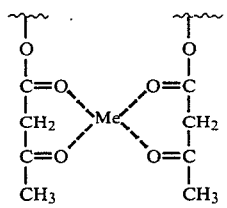

It is not necessary that the mixture is heated in all above-mentioned gelations. The gelation rapidly proceeds at room temperature to give transparent aqueous gels.

The aqueous gel according to the invention may include usual additives such as coloring agent, ultraviolet absorber, antioxidant, pH adjusting agent, and the like as occasion objects.

The gelation can proceed at room temperature for 2 to 3 sec in time of rapidity. Of course, the gelation time can be controlled by controlling kinds or the degree of acetoacetylation of the acetoacetylated high molecular compounds, kinds of the cross-linking agents, a proportion of the high molecular compound and cross-linking agent, concentrations of the aqueous solutions, pH of aqueous solutions, and the like.

The powdered acetoacetylated high molecular compound and the powdered cross-linking agent are mixed, water is added to the mixture in proper amount in times of necessity and the mixture is dissolved in water with stirring to give an aqueous gel. Also, when either of the two is aqueous solution, an aqueous gel can be obtained by only stirring the mixture.

According to the present invention, heating process necessary in case of using agar or carrageenan is not required and the aqueous solution of the mixture of the acetoacetylated high molecular compound and the cross-linking agent is merely stirred at room temperature to give a odorless, strong, elastic and transparent aqueous gel. The aqueous gel of the invention does not release water by freeze and thaw, storage at high temperature, or repeat of freezing and heating up to high temperature.

The hardness of the aqueous gel can be controlled with kinds of the cross-linking agents, a proportion of the cross-linking agents and the high molecular compound, concentrations of the aqueous solutions of the cross-linking agent and the high molecular compound, or pH of the aqueous solutions.

Therefore, the present invention can give from a soft aqueous gel having fluidity to a hard aqueous gel which is strong and elastic. Accordingly, the aqueous gel according to the invention can be widely used, for instance, a shock obsorber, a base material of medical plaster, a soundproofing material, a material for keeping cool or warm, medium for facillus, a gel entrapment of whole cells and enzymes, a sample of food or drink in show-window, and the like.

Next, the aqueous gel composition containing perfume or deodorant of the invention is explained.

The aqueous gel perfume or deodorant composition is prepared by including a perfume or deodorant component into the aqueous gel prepared by the above-mentioned process.

Examples of the perfumes are, for instance, a monoterpene hydrocarbon such as limonene, myrcene, carene, ocimene, pinene, camphene, terpinolene, tricytalene, terpinene, fenchene, phellandrene, sylvestrene, or savin; a sesquiterpene hydrocarbon such as caryophyllene, santalene, thujopsene, or cedrene; a diterpene hydrocarbon such as abietine or campholene; an aromatic hydrocarbon such as p-cymene or styrene; a carboxylic acid ester such as isoamyl acetate, geranyl acetate, citronelyl acetate, linalyl acetate, benzyl acetate, benzyl benzoate, benzyl salicinate, cinnamyl cinnamate, isoamyl undecylate, or cedryl acetate; a terpene alcohol such as linalol, citronellol or terpineol, a terpene aldehyde such as citral; and the like. A deodorant such as chlorine dioxide, lauryl methacrylate, geranyl crotonate or chlorophyll also can be employed.

As a process for containing the perfume into the aqueous gel, for instance, there are a process wherein the perfume is dissolved in an aqueous solution of surfactant, adding to the aqueous solution of acetoaceylated high molecular compound, to which the aqueous solution of the cross-linking agent is added; a process wherein 3 kinds of the above-mentioned aqueous solutions are mixed at the same time. Particularly, it is preferable that acetoacetylated polyvinyl alcohol is employed as the water-soluble acetoacetylated high molecular compound in the aqueous gel composition containing perfume. Examples of the surfactants are, for instance, a nonionic surfactant such as polyoxyethylene alkyl ether; an anionic surfactant such as sodium polyoxyethylene alkyl ether sulfate, and the like. These surfactant may be employed alone or in admixture thereof.

Acetoacetylated polyvinyl alcohol can be prepared by using polyvinyl alcohol and diketene in a usual manner. Polyvinyl alcohol obtained by hydrolysis reaction of polyvinyl acetate has a degree of polymerization of 200 to 3,000 and a degree of hydrolysis of 30 to 100% by mole. As the high molecular compound used in the invention, polyvinyl alcohol, derivatives of polyvinyl alcohol or a water-soluble hydrolysed copolymer of vinyl acetate and a monomer copolymerizable with vinyl acetate can be preferably employed. It is preferable that acetoacetylated polyvinyl alcohol has a degree of acetoacetylation of 0.5 to 20% by mole. When the degree of acetoacetylation is less than 0.5% by mole, it is hard to gel, and when the degree of acetoacetylation is more than 20% by mole, the acetoacetylated compound losses the solubility to water.

It is preferable that the concentration of the aqueous solution of acetoacetylated high molecular compound is 2 to 50% by weight in the aqueous gel composition as a solid matter. When the concentration is less than 2% by weight, it is hard to gel, and when the concentration is more than 50% by weight, even the acetoacetylated compound having low degree of polymerization cannot be dissolved to water.

The cross-linking agent is employed as 1 to 50% by weight aqueous solution. As the cross-linking agent used in the aqueous gel composition, there are used the above-mentioned compound containing amino group, compound containing hydrozino group and compound containing epoxy group. The cross-linking agent is employed alone or the admixture thereof. It is preferable that the cross-linking agent is 0.01 to 10% by weight in the aqueous gel composition as solid matter. When the concentration is less than 0.01% by weight, it is hard to gel and when the concentration is more than 10% by weight, the gelation proceedes too rapidly.

The aqueous gel composition of the present invention has following advantages.

(1) Even perfumes having a poor heat resistance is not deteriorated because the aqueous gel composition can gel at room temperature.

(2) The gelation time can be controlled at wide range by selecting the cross-linking agent.

(3) The aqueous gel composition is extremely excelent in transparency, so ornaments can be laid therein and colored and transparent articles can be obtained.

(4) The redissolution or serum-separation does not occur at a temperature of about 50° to about 80° C.

(5) The hardness of the gel is not changed and serum-separation does not occur at low temperature.

(6) It is not necessary that the composition is get into a vessel such as a glass vessel since the composition has the suitable rigidity.

In case that water-soluble alcohols are admixed together with a surfactant when the aqueous gel composition of the invention is prepared, the perfume or deodorant component of the composition is volatilized uniformly and little by little, and accordingly the effect of the composition is kept for a long period. Examples of the alcohols are, for instance, methyl alcohol, ethyl alcohol, isopropyl alcohol, ethylen glycol, propylene glycol, dipropylen glycol hexylene glycol, glycerol, 3-methyl-3-methoxybutanol and the like. These alcohols may be employed alone or in the admixture thereof.

When the water-soluble alcohols are included in the aqueous gel composition, there are a process in which the perfume or deodorant component is dissolved in the aqueous solution of the water-soluble alcohols and the surfactant, adding to the aqueous solution of acetoacetylated polyvinyl alcohol, to which the aqueous solution of the cross-linking agent is added; a process in which the perfume or deodorant component and the surfactant are dissolved into water, to which the water-soluble alcohols are added, and then the aqueous solution of acetoacetylated polyvinyl alcohol and finaly the aqueous solution of the cross-linking agent is added; a process in which the perfume or deodorant component, the surfactant, the water-soluble alcohols, the aqueous solution of acetoacetylated polyvinyl alcohol and the aqueous solution of the cross-linking agent are mixed at the same time. In accordance with the above-mentioned process, the aqueous gel composition having excellent transparency can be obtained.

It is preferable that a proportion used of the perfume or deodorant component is 1 to 15% by weight in the composition, a proportion used of the nonionic surfactant is 0.2 to 20% by weight based on the composition, a proportion used of the anionic surfactant is 0.1 to 5% by weight based on the composition and the proportion used of the water-soluble alcohols is 2 to 40% by weight based on the composition. When the proportion used of the perfume or deodorant component is less than 1% by weight, the composition is not practical and the proportion used of the perfume or deodorant component is more than 15% by weight, the perfume or deodorant component is not volatilized uniformly. When the proportion used of the nonionic surfactant is less than 0.2% by weight or the proportion used of the anionic surfactant is less than 0.1% by weight, not only the composition is cloudly since it is hard to dissolve the perfume component into water, but also the volatility of the perfume componet is poor. When the proportion used of the nonionic surfactant is more than 20% by weight or the proportion used of the anionic surfactant is more than 5% by weight, the perfume deteriolates. When the proportion used of the water-soluble alcohols is less than 2% by weight, the perfume component is not volatilized uniformly and when the proportion used of the alcohol is more than 40% by weight, the aqueous gel is cloudly or weak.

The aqueous gel composition of the invention may include usual additives such as antiseptic, an antifoaming agent, a ultraviolet absorber, or a coloring agent as occasion demands.

Next, the lubricant for metal-processing and the method for use thereof are explained.

The water-soluble acetoacetylated high molecular compound, particularly the acetoacetylated polyvinyl alcohol, and the cross-linking agent used in the lubricant of the invention are as described above. The compound and the cross-linking agent are employed as aqueous solutions having concentrations of 1 to 50% by weight, respectively. The aqueous solution of the water-soluble acetoacetylated high molecular compound, particularly acetoacetylated polyvinyl alcohol may include a solid lubricant such as graphite, tungsten disulfide, molybdenum disulfide or sodium fluoride as occasion demands.

The gelation mechanism of the aqueous solutions is as described above.

When the lubricant for metal-processing of the invention, there are some methods, e.g. a method in which the aqueous solution of the water-soluble acetoacetylated high molecular compound, particularly, acetoacetylated polyvinyl alcohol, is coated onto a surface of a metal material to be processed or a tool for metal-processing, e.g. mandrel or a steel plate rolled by a roller, and then the aqueous solution of the cross-linking agent is coated thereon; a method in which the aqueous solution of the cross-linking agent is coated onto the metal material, and then the aqueous solution of the water-soluble acetoacetylated high molecular compound, particularly, acetoacetylated polyvinyl alcohol, is coated thereon; or a method in which the aqueous solution of the water-soluble acetoacetylated high molecular compound and the aqueous solution of the cross-linking agent are coated with mixing them onto the metal material.

Thereby, a lubricous gel film is formed on the surface of the tool for metal-processing or the metal material to be processed to give the lubricity to the metal material.

The lubricant of the invention has the following advantages.

(1) The lubricous gel film is quickly formed even at low temperature, because the film is formed with chemical reaction.

(2) The film has an excellent water resistance.

(3) The film has an excellent friction resistance because the high molecular compound is cross-linked.

(4) The film has an excellent lubricity.

The present invention is more specifically described and explained by means of the following Examples, in which all parts and % are by weight unless otherwise noted. It is be understood that the present invention is not limited to Examples, and various changes and modifications may be made in the invention without departing from the spirit and scope thereof.

Examples 1 to 10 illustrate the process for preparing the aqueous gel of the present invention. Examples 11 to 25 illustrate the aqueous gel perfume or deodorant composition of the invention and Comparative Examples 1 to 3 illustrate the utilizing method of the conventinal perfume or deodorant gel, Preparation Examples 1 to 6 illustrate preparation of components of the lubricant for metal-processing, Examples 26 to 29 illustrate the utilizing method of the lubricant of the invention, and Comparative Examples 4 and 5 illustrate the utilizing method of the conventional lubricant.

EXAMPLE 1

To 90 parts of 10% aqueous solution of acetoacetylated polyvinyl alcohol having a degree of acetoacetylation of 5.5% by mole, a degree of hydrolysis of 99% by mole and a degree of polymerization of 1,100 was added 10 parts of 10% aqueous solution of N-β(aminoethyl)-γ-aminopropyltrimethoxysilane, and the mixture was stirred at room temperature. The mixture was poured into a vessel (100 mm×100 mm×25 mm) to give an aqueous gel having the excellent transparency.

The mixture before gelation had a pH of 9.3 and the gelation time was four minutes. The aqueous gel allowed to stand at room temperature for one week had a penetration of 3 mm (static load: 200 g/cm$^2$). The gel was allowed to stand in a freezer having a temperature of $-20°$ C. for 24 hours to freeze and then it was thawed at room temparature. The gel did not cause the serum-separation. The gel was allowed to stand in an oven having a temperature of 70° C. for 24 hours. The gel did not cause the serum-separation.

The results are shown in Table 1.

[Testing Method]

(1) Gelation time

The elased time when the viscosity of the mixture is 500 to 1000 cp measured by a Brookfield BL type viscosimeter (the mixture could not be stirred) after adding the cross-linking agent is shown.

(2) Transparency

The gel is observed with the naked eye.

Estimation:
O: Transparent
Δ: Semitransparent
X: Opaque (3) Penetration

A depth of penetration of a probe having a diameter of 4 mm into the aqueous gel allowed to stand for one week after adding the cross-linking agent is shown when a static load of 200 g/cm$^2$ is applied to the probe.

(4) Serum-separation (%)

Serum-separation is shown as a percentage of the weight of water separated from the 100 g of gel allowed to stand at sealed state under the predetermined condition to the weight of the initial gel (100 g).

(Serum-separation in freezing)

The aqueous gel is allowed to stand in a freezer having a temperature of $-20°$ C. for 24 hours to freeze and then the gel is thawed at room temperature.

(Serum-separation at hot temperature)

The aqueous gel is allowed to stand in a oven having a temperature of 70° C. for 24 hours.

EXAMPLES 2 TO 10

The procedure of Example 1 was repeated except that the following aqueous solution of the water-soluble acetoacetylated high molecular compound and the following aqueous solution of the cross-linking agent were used in proportions shown in Table 1.

The results are shown in Table 1.

[Aqueous solution of the water-soluble acetoacetylated high molecular compound]

PVA modified with AA: An aqueous solution of acetoacetylated polyvinyl alcohol employed in Example 1
HEC modified with AA: 2% aqueous solution of acetoacetylated hydroxyethyl cellulose having a degree of acetoacetylation of 4.1% by mole
MC modified with AA: 2% aqueous solution of acetoacetylated methyl cellulose having a degree of acetoacetylation of 5.2% by mole
CMC modified with AA: 2% aqueous solution of acetoacetylated carboxymethyl cellulose having a degree of acetoacetylation of 3.8% by mole
Starch modified with AA: 5% aqueous solution of acetoacetylated soluble starch having a degree of acetoacetylation of 4.3% by mole.

[Aqueous solution of cross-linking agent]

AEAPTMS: 10% aqueous solution of N-β(aminoethyl)-γ-aminopropyltrimethyoxysilane
GX: 10% aqueous solution of glyoxal
COHD: 5% aqueous solution of carboxyhydrazide
PPGGE: 10% aqueous solution of polypropyleneglycol glydicyl ether
MER: 10% aqueous solution of melamine resin
TAT: 10% aqueous solution of di-n-butoxybis(triethanolamine) titanate
TLA: 10% aqueous solution of titanium lactate

TABLE 1

| | High molecular compound | | Cross-linking agent | | pH of the mixture |
| --- | --- | --- | --- | --- | --- |
| | Kind | Amount (part) | Kind | Amount (part) | before gelation |
| Ex. 1 | PVA modified with AA | 90 | AEAPTMS | 10 | 9.3 |
| Ex. 2 | HEC modified with AA | 90 | GX | 10 | 5.0 |
| Ex. 3 | MC modified with AA | 95 | COHD | 5 | 5.1 |
| Ex. 4 | CMC modified with AA | 90 | PPGGE | 10 | 5.2 |
| Ex. 5 | Starch modified with AA | 98 | MER | 2 | 7.2 |
| Ex. 6 | PVA modified with AA | 90 | TAT | 10 | 5.1 |
| Ex. 7 | HEC modified with AA | 90 | TLA | 10 | 5.2 |
| Ex. 8 | MC modified with AA | 95 | AEAPTMS | 5 | 8.1 |
| Ex. 9 | CMC modified with AA | 90 | GX | 10 | 4.9 |
| Ex. 10 | Starch modified with AA | 95 | COHD | 5 | 5.2 |

| | Penetration | Serum-seperation in freezing | Serum-separation at hot temperature |
| --- | --- | --- | --- |

TABLE 1-continued

|        | Gelation time | Transparency | (mm) | (%) | (%) |
|--------|---------------|--------------|------|-----|-----|
| Ex. 1  | 2 minutes     | O            | 3    | 0   | 0   |
| Ex. 2  | 10 hours      | O            | 6    | 0   | 0   |
| Ex. 3  | 20 seconds    | O            | 5    | 0.1 | 0   |
| Ex. 4  | 2 days        | O            | 40   | 0   | 0   |
| Ex. 5  | 3 days        | O            | 45   | 0.2 | 0   |
| Ex. 6  | 2 hours       | O            | 36   | 0   | 0   |
| Ex. 7  | 8 hours       | O            | 23   | 0   | 0   |
| Ex. 8  | 5 minutes     | O            | 8    | 0   | 0   |
| Ex. 9  | 16 hours      | O            | 14   | 0   | 0   |
| Ex. 10 | 30 seconds    | O            | 11   | 0.1 | 0   |

EXAMPLE 11

To 60 parts of 10% aqueous solution of acetoacetylated polyvinyl alcohol having a degree of acetoacetylation of 5% by mole, a degree of hydrolysis of 88% by mole, and a degree of polymerization of 1000 was added 4 parts of polyoxyethylene alkyl ether (HLB: 13.8) as a nonionic surfactant, 2 parts of sodium polyoxyethylene alkylether sulfate as an anionic surfactant, 6 parts of benzyl acetate, 10 parts of 10% aqueous solution of glyoxal and 18 parts of water and the mixture was uniformly stirred. Then the mixture was allowed to stand for 5 hours at room temperature to give an aqueous gel composition containing perfume.

EXAMPLE 12

The procedure of Example 11 was repeated except that 10 parts of 4% aqueous solution of adipic acid dihydrazide was employed instead of 10 parts of 10% aqueous solution of glyoxal and the mixture was allowed to stand for 5 minutes at room temperature to give an aqueous gel composition containing perfume.

EXAMPLE 13

The procedure of Example 11 was repeated except that 10 parts of 10% aqueous solution of polyethyleneimine was employed instead of 10 parts of 10% aqueous solution of glyoxal and the mixture was allowed to stand at room temperature for 1 minute to give an aqueous gel composition containing perfume.

EXAMPLE 14

The procedure of Example 11 was repeated except that 10 parts of 10% aqueous solution of polyethylene glycol glycidyl ether was employed instead of 10 parts of 10% aqueous solution of glyoxal and the mixture was allowed to stand at room temperature for 3 days to give an aqueous gel composition containing perfume.

EXAMPLE 15

The procedure of Example 11 was repeated except that 90 parts of 2% aqueous solution of acetoacetylated hydroxyethyl cellulose having a degree of acetoacetylation of 5.1% by mole was employed instead of 60 parts of 10% aqueous solution of acetoacetylated polyvinyl alcohol and the mixture was allowed to stand at room temperature for 24 hours to give an aqueous gel composition containing perfume.

EXAMPLE 16

The procedure of Example 12 was repeated except that 90 parts of 2% aqueous solution of acetoacetylated methyl cellulose having a degree of acetoacetylation of 4.4% by mole was employed instead of 60 parts of 10% aqueous solution of acetoacetylated polyvinyl alcohol and the mixture was allowed to stand at room temperature for 10 minutes to give an aqueous gel composition containing perfume.

EXAMPLE 17

The procedure of Example 13 was repeated except that 90 parts of 2% aqueous solution of acetoacetylated carboxymethyl cellulose having a degree of acetoacetylation of 3.6% by mole was employed instead of 60 parts of 10% aqueous solution of acetoacetylated polyvinyl alcohol and the mixture was allowed to stand at room temperature for 2 minutes to give an aqueous gel composition containing perfume.

EXAMPLE 18

The procedure of Example 14 was repeated except that 80 parts of 5% aqueous solution of acetoacetylated soluble starch having a degree of acetoacetylation of 4.1% by mole was employed instead of 60 parts of 10% aqueous solution of acetoacetylated polyvinyl alcohol and the mixture was allowed to stand at room temperature for 2 days to give an aqueous gel composition containing perfume.

COMPARATIVE EXAMPLE 1

To 85.3 parts of water was added 6 parts of benzyl acetate, 2.5 parts of carrageenan, 0.2 parts of locust bean gum, 4 parts of polyoxyethylene alkyl ether (HLB: 13.8) as a nonionic surfactant and 2 parts of sodium polyoxyethylene alkylether sulfate as an anionic surfactant and the mixture was heated at 70° to 80° C. for 1 hour to disperse uniformly. Then the dispersion was allowed to stand at room temperature for 1 hour to give an aqueous gel composition containing perfume.

TEST EXAMPLE

With respect to the aqueous gel compositions obtained in Examples 11 to 18 and in Comparative Example 1, the transparency, the heat resistance, the low-temperature resistance and the deterioration of perfume were estimated.

The results are shown in Table 2.

TABLE 2

|         | Transparency | Heat resistance | Low-temperature resistance | Deterioration of perfume |
|---------|--------------|-----------------|----------------------------|--------------------------|
| Ex. 11  | O            | O               | O                          | O                        |
| Ex. 12  | O            | O               | O                          | O                        |
| Ex. 13  | O            | O               | O                          | O                        |
| Ex. 14  | O            | O               | O                          | O                        |
| Ex. 15  | O            | O               | O                          | O                        |
| Ex. 16  | O            | O               | O                          | O                        |
| Ex. 17  | O            | O               | O                          | O                        |
| Ex. 18  | Δ            | O               | O                          | O                        |
| Com. Ex. 1 | X         | X               | X                          | X                        |

[Testing Method]

(1) Transparency

The aqueous gel composition is observed with the naked eye.
Estimation:
O: Uniformly transparent
Δ: Semitransparent and cloudy
X: Opaque

(2) Heat resistance

The aqueous gel composition is allowed to stand at 70° C. for 24 hours and then a percentage of water-release is measured.
Estimation:
O: A percentage of serum-separation of less than 1%
Δ: A percentage of serum-separation of 1 to 10%
X: A percentage of serum-separation of more than 10%

(3) Low-temperature resistance

The aqueous gel composition is allowed to stand at −20° C. for 24 hours then at room temperature for 24 hours and a percentage of serum-separation is measured.
Estimation:
O: A percentage of serum-separation of less than 1%
Δ: A percentage of serum-separation of 1 to 10%
X: A percentage of serum-separation of more than 10%

(4) Deterioration of perfume

The aqueous gel is estimated by an organoleptic test.
Estimation:
O: Perfume is not deteriorated at all.
Δ: Perfume is deteriorated a little.
X: Perfume is deteriorated.

EXAMPLE 19

To 8 parts of a mixture of perfumes having a smell of fragrant olive was added 5 parts of polyoxyethylene nonyl phenyl ether (HLB: 14.5) as a nonionic surfactant and 7 parts of 25% aqueous solution of sodium sulphate of polyoxyethylene alkyl phenyl ether as an anionic surfactant and the mixture was uniformly stirred. Then, there are added in order 4 parts of water, 12 parts of ethylene glycol, 60 parts of 10% aqueous solution of acetoacetylated polyvinyl alcohol having a degree of acetoacetylation of 5% by mole, a degree of hydrolysis of 88% by mole and a degree of polymerization of 1000 and 4 parts of 5% aqueous solution of adipic acid hydrazide to give a uniform mixture. The mixture was allowed to stand at room temperature for 10 minutes to give an aqueous gel composition containing perfume.

EXAMPLES 20 TO 25

The procedure of Example 19 was repeated except that an acetoacetylated polyvinyl alcohol, water, a nonionic surfactant, an anionic surfactant, water-soluble alcohols and a cross-linking agent were employed in amounts and kinds shown in Table 3 to give an aqueous gel composition containing perfume.

COMPARATIVE EXAMPLE 2

The procedure of Example 19 was repeated except that an anionic surfactant was not employed to give an aqueous gel composition containing perfume.

COMPARATIVE EXAMPLE 3

The Example 22 was repeated except that ethylene glycol was not employed to give an aqueous gel composition containing perfume.

TEST EXAMPLE

With respect to the aqueous gel composition containing perfume, the transparency, the percentage of serum-separation, the state of surface, and the volatility (power of perfume) are estimated.
The results are shown in Table 3.

[Testing Method]

(1) Transparency

The aqueous gel composition is observed with the naked eye.
Estimation
O: Transparent
X: Opaque

(2) Percentage of serum-separation (%)

The aqueous gel composition is allowed to stand at −10° C. for 24 hours and then at 50° C. for 24 hours. The above-mentioned procedure was repeated 5 times and a percentage of serum-separation is measured.

(3) State of surface

A surface of the aqueous gel composition allowed to stand at 20° C. in 65% RH for one month is observed with the naked eye.
Estimation:
S: Film is not formed on the surface of the composition and the surface of the composition is soft.
H: Film is formed on the surface of the composition and the surface of the composition is hard.

(4) Volatility (Power of perfume)

The aqueous gel composition is allowed to stand at 20° C. in 65% RH for one month and then the power of perfume is estimated.
Estimation:
O: Perfume of the composition is enoughly maintained.
X: Power of perfume is remarkably lowered.

TABLE 3

| | Ex. 19 | Ex. 20 | Ex. 21 | Ex. 22 | Ex. 23 | Ex. 24 | Ex. 25 | Com. Ex. 2 | Com. Ex. 3 |
|---|---|---|---|---|---|---|---|---|---|
| 10% Aqueous solution of acetoacetylated polyvinyl alcohol (part) | 60 | 60 | 60 | 50 | 60 | 70 | 60 | 60 | 60 |
| Nonionic surfactant (part) | | | | | | | | | |

TABLE 3-continued

| | Ex. 19 | Ex. 20 | Ex. 21 | Ex. 22 | Ex. 23 | Ex. 24 | Ex. 25 | Com. Ex. 2 | Com. Ex. 3 |
|---|---|---|---|---|---|---|---|---|---|
| Polyoxyethylene nonyl phenyl ether (HLB = 14.5) | — | 4 | — | — | — | — | 4 | — | — |
| Polyoxyethylene octyl phenyl ether (HLB = 13.1) | 5 | — | — | 5 | 10 | — | — | 5 | 5 |
| Addition product of hydrogenated castor oil and ethyleneoxide (HLB = 14.8) | — | — | 6 | — | — | 4 | — | — | — |
| Anionic surfactant (part) | | | | | | | | | |
| 25% aqueous solution of sodium sulphate of polyoxyethylene alkyl phenyl ether | 7 | — | 6 | — | — | 4 | — | — | — |
| 25% aqueous solution of sodium sulphate of polyoxyethylene alkyl ether | — | 8 | — | 7 | 2 | — | 8 | — | 7 |
| Mixture of perfume | 8 | 8 | 8 | 8 | 8 | 8 | 8 | 8 | 8 |
| Cross-linking agent (part) | | | | | | | | | |
| 5% aqueous solution of adipic acid dihydrazide | 4 | — | — | — | 4 | — | — | 4 | — |
| 10% aqueous solution of polyethyleneimine | — | 4 | — | — | — | 4 | — | — | — |
| 10% aqueous solution of glyoxal | — | — | 4 | 4 | — | — | — | — | 4 |
| Polyethylene glycol diglycidyl ether | — | — | — | — | — | — | 0.3 | — | — |
| Water (part) | 4 | 10 | 14 | 4 | 4 | 4 | 7.7 | 11 | 16 |
| Water-soluble alcohols (part) | | | | | | | | | |
| Hexylene glycol | — | 6 | — | — | — | 6 | — | — | — |
| Ethylene glycol | 12 | — | — | 12 | — | — | — | 12 | — |
| Propylene glycol | — | — | 12 | — | — | — | 12 | — | — |
| Glycerol | — | — | — | — | 12 | — | — | — | — |
| Gelation time (minute) | 10 | 5 | 240 | 220 | 10 | 270 | 7200 | 270 | 220 |
| Transparency | O | O | O | O | O | O | O | X | O |
| Percentage of serum-separation (%) | 0.6 | 1.2 | 0.4 | 0.4 | 0.3 | 0.1 | 0.5 | 7.5 | 15.2 |
| State of surface | S | S | S | S | S | S | S | S | H |
| Volatility | O | O | O | O | O | O | O | O | X |

As apparent from Table 3, the aqueous gel composition of the present invention is excellent in transparency, percentage of serum-separation, state of surface and volatility.

The aqueous gel composition obtained in Comparative Example 2 (The composition was prepared in the same manner as in Example 19 except that an anionic surfactant was not employed.) is remarkably low in the percentage of serum-separation and is poor in transparency. The aqueous gel composition obtained in Comparative Example 3 (The composition was prepared in the same manner as in Example 22 except that water-soluble alcohols were not employed.) is hard in the state of surface and accordingly is remarkably low in the volatility. Also the composition is remarkably low in the percentage of serum-separation.

PREPARATION EXAMPLE 1

[Preparation of aqueous solution of PVA modified with AA]

There was prepared 10% aqueous solution of acetoacetylated polyvinyl alcohol having a degree of acetoacetylation of 5% by mole, a degree of hydrolysis of 88% by mole and a degree of polymerization of 1,000 (hereinafter referred to as "PVA solution of Preparation Example 1").

PREPARATION EXAMPLE 2

[Preparation of alkaline aqueous solution of PVA modified with AA]

A pH of the PVA solution of Preparation Example 1 was adjusted with aqueous ammonium to give an aqueous solution of PVA modified with AA having a pH of 9 (hereinafter referred to as "PVA solution of Preparation Example 2").

PREPARATION EXAMPLE 3

[Preparation of aqueous solution of PVA modified with AA containing solid lubricant]

To 100 parts of PVA solution of Preparation Example 1 was added 20 parts of powdered graphite having a particle size of about 100 μm and the mixture was stirred to give an aqueous solution of PVA modified with AA contianing solid lubricant (hereinafter referred to as "PVA solution of Preparation Example 3").

PREPARATION EXAMPLE 4

[Preparation of cross-linking containing aldehyde group]

There was prepared 10% aqueous solution of glyoxal.

PREPARATION EXAMPLE 5

[Preparation of cross-linking containing hydrazino group]

There was prepared 4% aqueous solution of adipic acid hydrazide.

PREPARATION EXAMPLE 6

[Preparation of cross-linking agent containing hydrazino group]

There was prepared 10% aqueous solution of polyethyleneimine.

EXAMPLE 26

The PVA solution of Preparation Example 2 was coated on a surface of a steel plate having a thinkness of 0.1 mm and then a aqueous solution of cross-linking agent containing aldehyde group prepared in Preparation Example 4 was sprayed thereon to give a lubricous gel film having excellent water-resistance in a very short time, i.e. about 10 seconds. Then, the steel plate was cold-rolled. The adhesion of the film gel was excellent.

EXAMPLE 27

The PVA solution of Preparation Example 3 was coated on a surface of a steel plate and then the aqueous solution of cross-linking agent containing hydrazino group was sprayed thereon to form a lubricant gel film at room temperature. Then, the steel plate was immediately cold-rolled.

The results are shown in Table 4.

EXAMPLE 28

The aqueous solution of cross-linking agent containing amino group was coated on a surface of a steel plate and then the PVA solution of Preparation Example 1 was sprayed thereon to form a lubricous gel film at room temperature. The steel plate was immediately cold-rolled.

The results are shown in Table 4.

COMPARATIVE EXAMPLES 4 AND 5

A mixture of graphite and oil (Comparative Example 4) and a mixture of graphite and ethylene-vinyl acetate copolymer emulsion (Comparative Example 5) were coated on a surface of a steel plate, respectively.

The steel plates were immediately cold-rolled.

The results are shown in Table 4.

TABLE 4

|  | Film-forming time | Lubricity | Adhesion |
| --- | --- | --- | --- |
| Ex. 26 | O | O | O |
| Ex. 27 | O | O | O |
| Ex. 28 | O | O | O |
| Com. Ex. 4 | Δ | O | X |
| Com. Ex. 5 | X | O | O |

[Estimation]

(1) Film-forming time

O: Less than 60 seconds
Δ: From 60 seconds to 5 minutes
X: More than 5 minutes (2) Lubricity O: The surface of the plate is not baked.
Δ: The surface of the plate is baked a little.
X: The surface of the plate is baked.

(3) Adhestion

After rolling the steel plate coated with the lubricant, it is observed whether the film is peeled off or not.
O: Film is not peeled off.
Δ: Film is peeled off a little.
X: Film is peeled off largely.

EXAMPLE 29

A mixture of the PVA solution of Preparation Example 3 and the aqueous solution of cross-linking agent of Preparation Example 6 was sprayed on a mandrel having high temperature in a Mannesmann mandrel mill used for preparing a jointless tube during tempering. Immediately, the gelation was caused to prepare a dry and water repellet film on the surface of the mandrel.

The mandrel on which the film was coated was dipped in water to cool, but the film was not peeled away.

The PVA solution of Preparation Example 3 and then the aqueous solution of the cross-linking agent of Preparation Example 6 was sprayed on a new mandrel. Immediately, the gelation was caused at room temperatue to give a water repellent film on the surface of the mandrel.

By using the lubricant of the present invention, the abrasion of the mandrel is decreased and a tube can be wound uniformly around the mandrel. Accordingly, the quality of the tube can be improved and a tube having a thin thickness can be prepared.

What we claim is:

1. A process for preparing an aqueous gel which comprises mixing at least one water-soluble acetoacetylated high molecular compound selected from the group consisting of acetoacetylated polyvinyl alcohol, acetoacetylated hydroxyethyl cellulose, acetoacetylated hydroxypropyl cellulose, acetoacetylated methyl cellulose, acetoacetylated carboxymethyl cellulose and acetoacetylated starch, at least one cross-linking agent selected from the group consisting of a compound containing an amino group, a compound containing an aldehyde group, a compound containing a hydrazino group, a compound containing an epoxy group, a compound containing a methylol group, a metal alkoxide and a metal chelate and water, thereby cross-linking said high molecular compound to form an aqueous gel.

2. The process of claim 1, wherein said metal is a member selected from the group consisting of titanium, zirconium and aluminium.

3. An aqueous gel composition containing perfume or deodorant comprising an aqueous gel prepared by mixing at least one water-soluble acetoacetylated high molecular compound selected from the group consisting of acetoacetylated polyvinyl alcohol, acetoacetylated hydroxyethyl cellulose, acetoacetylated hydroxypropyl cellulose, acetoacetylated methyl cellulose, acetoacetylated carboxymethyl cellulose and acetoacetylated starch, at least one cross-linking agent selected from the group consisting of a compound containing an amino group, a compound containing an aldehyde group, a compound containing a hydrazino group, a compound containing an epoxy group, a compound containing a methylol group, a metal alkoxide and a metal chelate and water, thereby cross-linking said high molecular compound to form an aqueous gel and a perfume or deodorant component.

4. The composition of claim 2, wherein said metal is a member selected from the group consisting of titanium, zirconium and aluminium.

5. The composition of claim 5, wherein said composition comprises
2 to 50% by weight of acetoacetylated polyvinyl alcohol,
0.01 to 10% by weight of at least one member selected from the group consisting of a compound containing an amino group, a compound containing an aldehyde group, a compound containing a hydrazino group and a compound containing an epoxy group, and
40 to 97.99% by weight of water.

6. An aqueous gel composition containing perfume or deodorant comprising (a) 20 to 96.7% by weight of an aqueous gel prepared from a mixture of 2 to 15% by weight of at least one water-soluble acetoacetylated high molecular compound selected from the group consisting of acetoacetylated polyvinyl alcohol, acetoacetylated hydroxyethyl cellulose, acetoacetylated hydroxyproplyl cellulose, acetoacetylated methyl cellulose, acetoacetylated carboxymethyl cellulose and acetoacetylated starch, 0.01 to 3% by weight of at least one member selected from the group consisting of a compound containing an aldehyde group, a compound containing a hydrazino group, a compound containing an amino group and a compound containing an epoxy group and 82 to 97.99% by weight of water, (b) 1 to 15% by weight of a perfume component, (c) 0.2 to 20% by weight of a nonionic surfactant, (d) 0.1 to 5% by weight of an anionic surfactant and (e) 2 to 40% by weight of water-soluble alcohols.

7. A lubricant for metal-processing comprising (A) an aqueous solution of at least one water-soluble acetoacetylated high molecular compound selected from the group consisting of acetoacetylated polyvinyl alcohol, acetoacetylated hydroxyethyl cellulose, acetoacetylated hydroxypropyl cellulose, acetoacetylated methyl cellulose, acetoacetylated carboxymethyl cellulose and acetoacetylated starch and (B) an aqueous solution of at least one member selected from the group consisting of a compound containing an aldehyde group, a compound containing a hydrazino group and compound containing an amino group.

8. The lubricant of claim 7, wherein said component (A) includes a solid lubricant.

9. A method for use of a lubricant comprising (A) an aqueous solution of at least one water-soluble acetoacetylated high molecular compound selected from the group consisting of acetoacetylated polyvinyl alcohol, acetoacetylated hydroxyethyl cellulose, acetoacetylated hydroxypropyl cellulose, acetoacetylated methyl cellulose, acetoacetylated carboxymethyl cellulose and acetoacetylated starch and (B) an aqueous solution of at least one member selected from the group consisting of a compound containing an aldehyde group, a compound containing a hydrazino group and a compound containing an amino group; which comprises coating either of said component (A) or said component (B) onto a surface of a metal substrate, and then coating the other thereon.

10. The method of claim 9, wherein said aqueous solution of water-soluble acetoacetylated high molecular compound includes a solid lubricant.

11. The method of claim 9, wherein said metal substrate is a tool for metal-processing or a metal material to be processed.

12. The method of claim 9, wherein a mixture of said component (A) and said component (B) is coated onto said metal substrate.

* * * * *